United States Patent
Futterknecht

(10) Patent No.: US 6,558,125 B1
(45) Date of Patent: May 6, 2003

(54) INJECTOR FOR APPLYING FLUIDS FITTED WITH A PRESSURE MEASURING SYSTEM

(75) Inventor: Hans-Dieter Futterknecht, Ulm (DE)

(73) Assignee: Ulrich GmbH & Co. KG, Ulm (DE)

( * ) Notice: Subject to any disclaimer, the term of this patent is extended or adjusted under 35 U.S.C. 154(b) by 0 days.

(21) Appl. No.: 09/646,250
(22) PCT Filed: Nov. 27, 1999
(86) PCT No.: PCT/DE99/03794
§ 371 (c)(1),
(2), (4) Date: Sep. 13, 2000
(87) PCT Pub. No.: WO00/41747
PCT Pub. Date: Jul. 20, 2000

(30) Foreign Application Priority Data

Jan. 13, 1999 (DE) .......................... 199 00 937

(51) Int. Cl.⁷ ......................... F04B 49/00; F04B 49/06; A61M 1/00
(52) U.S. Cl. ......................... 417/1; 417/44.2; 417/44.9; 604/118
(58) Field of Search ........................ 417/1, 44.2, 44.9; 604/118

(56) References Cited

U.S. PATENT DOCUMENTS

| | | | | |
|---|---|---|---|---|
| 4,710,166 A | * | 12/1987 | Thompson et al. | 604/81 |
| 4,795,440 A | * | 1/1989 | Young et al. | 604/122 |
| 5,693,008 A | * | 12/1997 | Brugger et al. | 604/4.01 |
| 5,882,339 A | * | 3/1999 | Beiser et al. | 604/153 |
| 6,488,660 B1 | * | 12/2002 | Futterknecht | 604/129 |

* cited by examiner

Primary Examiner—Charles G. Preay
Assistant Examiner—Michael K. Gray
(74) Attorney, Agent, or Firm—Herbert Dubno

(57) ABSTRACT

The injector of the invention serves for applying contrast media for X-ray or nuclear spin tomography and has a tube (3), as well as a roller pump (7) surrounded at least partially in peripheral direction by the tube (3) for transporting the fluid from a storage vessel (2) to a cannula. A pressure chamber (10) connected with the interior of the tube (3) through an opening (9) in the tube wall is provided, which has a component (11) adjustable under the effect of the fluid pressure, acting upon a pressure sensor (12).

11 Claims, 3 Drawing Sheets

Figure 1:
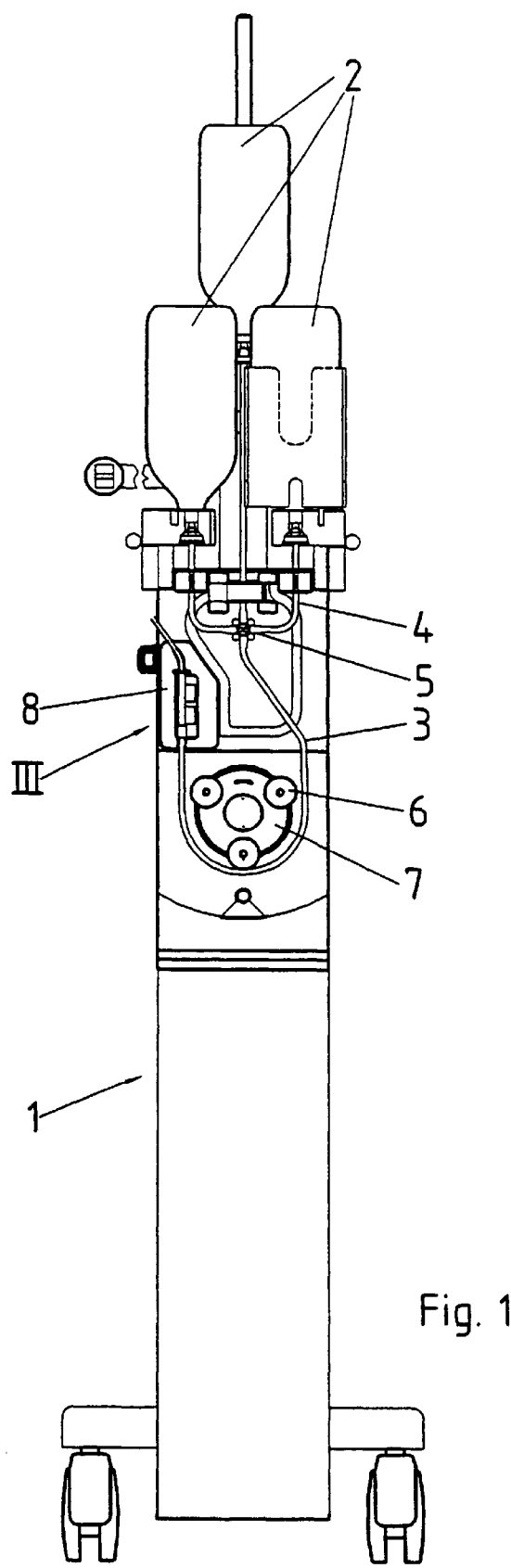

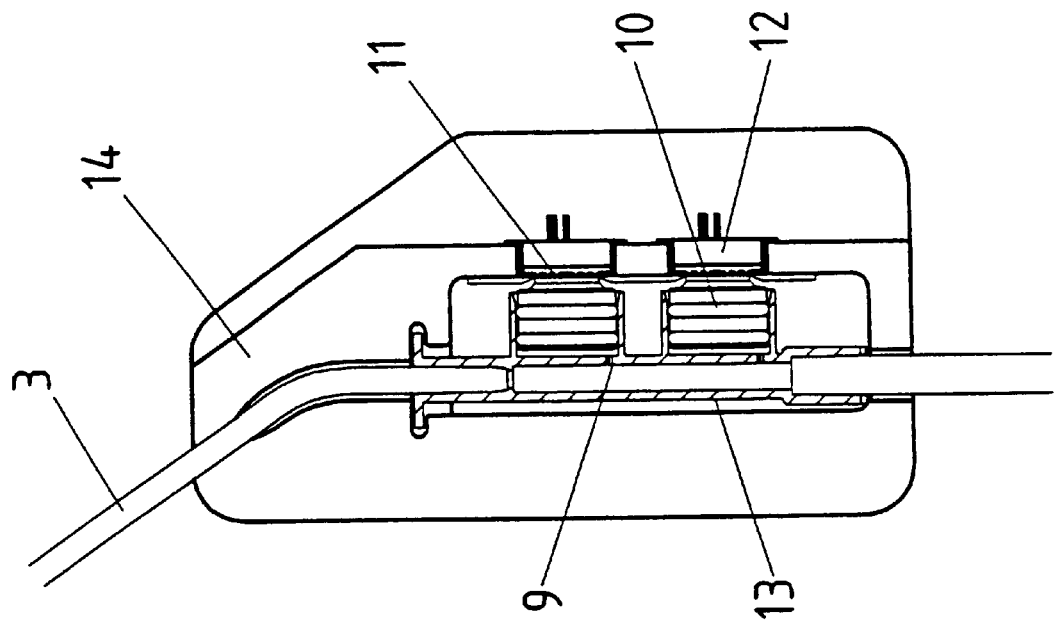
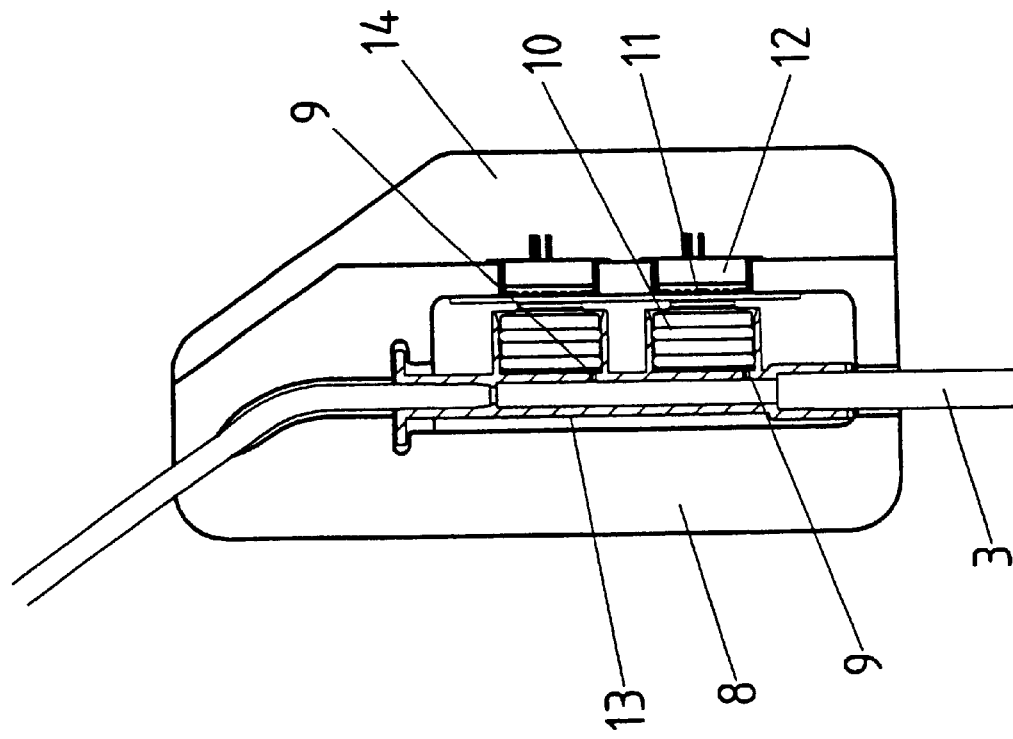

INJECTOR FOR APPLYING FLUIDS FITTED WITH A PRESSURE MEASURING SYSTEM

BACKGROUND OF THE INVENTION

The invention relates to an injector for applying fluids, particularly contrast media for x-ray or nuclear-spin tomography, with a tube, as well as a roller pump, at least partially surrounded by the tube in peripheral direction, for the transport of the fluid from a storage vessel to a cannula.

In such injectors known from practice roller pumps are used for the transport of the fluid in the tube from the storage vessel to a patient, without direct contact, thereby insuring sterility. However there have been problems because the roller pump does not work free of slippage and the output depends on the counterpressure so that, particularly when unsuitable cannulas with a diameter which is too small are used, the amount of fluid required for the examination is not injected to the patient, although the roller pump works with the selected predetermined drive output, respectively rotations per minute.

SUMMARY OF THE INVENTION

It is therefore the object of the invention to develop an injector of the kind mentioned in the introduction, which during the application of fluids insures at all times that the patient receives the amount of fluid required for the examination.

This task is achieved in an injector of the aforementioned kind by providing a pressure chamber connected with the tube interior through an opening in the tube wall, having a component which can be adjusted under the effect of the fluid pressure and which acts upon a pressure sensor.

This invention offers the advantage that the flow rate of the fluid does not have to be measured directly, since it has been found that below a certain pressure threshold value, there is a sufficiently linear interrelationship between the output of the roller pump and its rotary speed, so that it is sufficient to monitor the pressure ratio in order to insure that the pressure value threshold is not surpassed. It has also to be noted that the sterility of the fluid is furthermore insured while the pressure is measured, because there is no direct contact of the fluid with the pressure sensor, since the pressure ratio is being transmitted to the latter by the adjustable component.

In a roller pump one roller is in contact with the elastically deformable tube and deforms the same, in order to transport the downstream located fluid column further upstream in the rotation direction of the pump. However the elasticity of the tube influences the precision of the pressure measurement, so that, according to a further development of the invention, it is provided that between two segments of the tube a rigid pipe with an opening be inserted, to which the pressure chamber is fastened.

An embodiment distinguished by the simplicity of its construction is characterized in that the adjustable component consists of a liquid-proof elastic membrane. This elastic membrane in contact with the pressure sensor stretches under increasing pressure, respectively shrinks back under falling pressure, a fact communicated to the pressure sensor, which based on the changes of the membrane can determine the pressure ratio.

If sufficient measuring accuracy is required over a longer measuring interval, it is advantageous to design the adjustable component as a piston, which acts upon the pressure sensor with a prop tightened against the bottom plate of the pressure chamber. In this embodiment there is no limitation of the adjustment range of the prop, respectively piston, stipulated in principle, so that measurements can be performed over a longer pressure interval.

The same advantage exists also when the adjustable component is a piston tightened against the pressure chamber wall, which acts directly upon the pressure sensor, whereby in this embodiment the simplicity of the construction is further enhanced.

Since the injector is intended for use in the medical field, there are high requirements for its reliability. Since the detection of the pressure ratio with the pressure-measuring system is to be conceived as a safety feature, it is advantageous when the pressure chamber and the associated pressure sensor are doubled, the safety devices being this way laid out to be redundant.

In principle it is sufficient when the pressure chamber is connected through a single opening in the tube wall with the tube interior, since according to the principle of communicating tubes, pressure changes inside the tube would be transmitted also to the pressure chamber, in that for instance fluid would flow into the pressure chamber when the pressure rises and when it falls the flow direction would reverse itself. However if only one opening is available, it can take a relatively long time until the ratios have again stabilized after a pressure change, so that the time resolution would be relatively minimal. In order to improve the latter, it is provided that several openings of the tube wall are assigned to the pressure chamber. In the case of several openings the fluid not only flows into the pressure chamber and remains there stationarily at constant pressure ratios, but a flow passes through the pressure chamber, where through one opening the fluid flows into the pressure chamber and exits through another opening, so that the pressure-measuring system can follow the pressure changes more promptly. It is also advantageous that the fluid in the pressure chamber is constantly exchanged, so that when a fluid is changed, for instance from one contrast medium to another or to a rinsing solution, there are no residues of the previous fluid in the tube.

It has also proven to be advantageous when the pressure chamber is arranged on the cannula-side end of the tube, since concurrently with the pressure measurement also a detection of the seal tightness of the upstream portion of the tube can take place, therefore suitably the pressure chamber is arranged as far upstream as possible.

In order to test the function capability and the integrity of the pressure-measuring system, it is favorable when the tube with the pressure chamber and the pressure sensor passes through a container, wherein a wetness sensor is arranged as a leak detector.

According to a particularly advantageous embodiment it is further provided that the pressure sensor consists of an electric pressure receiver, since this way the pressure sensor not only indicates the pressure value at a particular moment, but also creates the possibility of a further evaluation of the signal of the electric pressure receiver, for which purpose an evaluation unit controlling the rotary pump speed is provided for the electric signals sent by the electric pressure receiver.

BRIEF DESCRIPTION OF THE INVENTION

Figure 2:
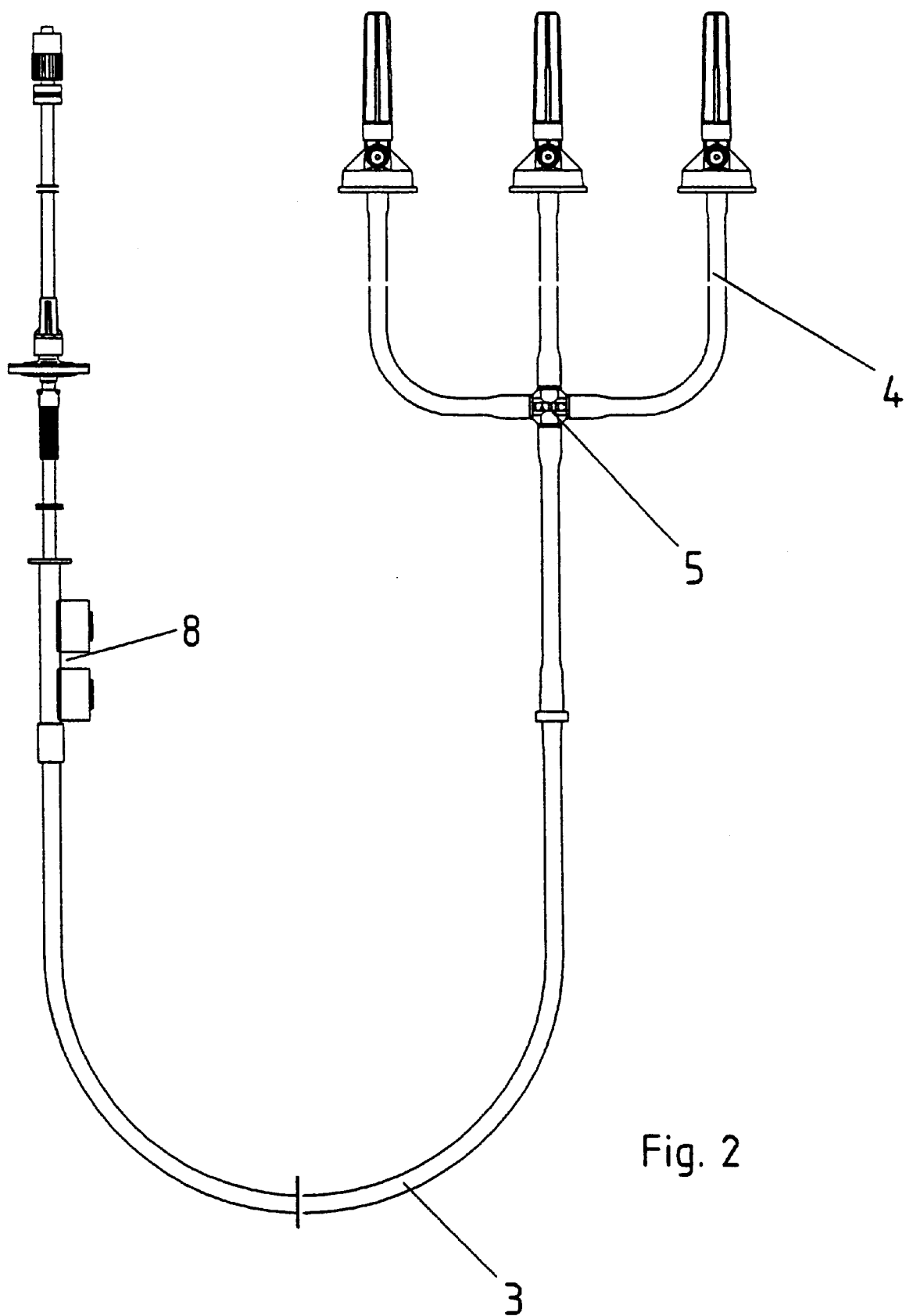

Subsequently the invention is closer described with reference to an embodiment example represented in the drawing; it shows:

FIG. 1 a front view in a schematic representation of the injector of the invention, FIG. 2 the tube system used in the injector with the upstream arranged pressure-measuring system, FIG. 3 the detail III in FIG. 1, namely the pressure-measuring system with pressure-less pressure chambers, and FIG. 4 a representation of the pressure chambers according to FIG. 3 filled at maximal pressure.

DETAILED DESCRIPTION

FIG. 1 shows a frontal view of an injector 1, which has a mounting for several storage vessels 2 connected via connection tubes 4 and a branch segment 5 provided with clampable stop valves with a tube 3, which partially surrounds in peripheral direction a roller pump 7 having three rollers 6. The injector 1 serves for delivering a fluid, particularly a contrast medium for X-ray or nuclear spin tomography examinations to a patient, from a storage vessel 2 by means of the roller pump 7 through the tube 3. In order to insure thereby that the correct amount of fluid is injected to the patient, the injector 1 is associated with a pressure-measuring system 8, by means of which the pressure inside the tube 3 can be determined. This pressure-measuring system 8 is formed by at least one opening 9 in the tube walling, through which the interior of tube 3 is connected to a pressure chamber 10, which has a component 11 adjustable under the effect of the fluid pressure, which acts upon a pressure sensor 12 designed as an electric pressure receiver.

This pressure-measuring system 8 is represented in FIGS. 3 and 4 as an enlarged detail of FIG. 1. Between two sections of the tube 3, at its downstream end a rigid pipe 13 is inserted with the opening 9 leading into the pressure chamber 10 fastened to the pipe 13. It has to be noted that the pressure-measuring system 8 with the pressure chamber 10 and the pressure sensor 12, as well as the adjustable component 11, are provided twice as shown in FIGS. 3 and 4.

If by means of the roller pump 7 the fluid is transported through the tube 3 to and through the rigid pipe 13, the fluid enters the interior of the pressure chamber 10 through the opening 9, when the pressure inside the tube is higher than in the pressure chamber 10. If the pressure increases further, then the adjustable component 11, which can be either a liquid-proof elastic membrane or a piston acting upon the pressure sensor 12 with a prop tightened against the pressure chamber 10, is reset, whereby a higher pressure acts upon the pressure sensor 12. If the pressure falls inside the tube 3, respectively the rigid pipe 13, then the fluid flows back from the interior of the pressure chamber 10 through the opening 9, which results in the falling of the pressure at the pressure sensor 12. If the pressure chamber 10 has two openings 9, then the pressure chamber 10 is continuously traversed by the flow of fluid, which is exchanged not only when a change in the pressure ratio occurs in the pressure chamber 10.

In order to avoid a limitation of the adjustment range of the adjustable component 11, such as system-conditioned in the case of the elastic membrane, it is also possible to design the adjustable component 11 as a piston which tightened against the pressure chamber wall, which acts directly upon the pressure sensor 12, which has the advantage of a simpler construction compared to the embodiment with a piston and a tightened prop.

The tube 3 and the rigid pipe 13 are passed through a container 14, wherein the pressure-measuring system 8 with pressure chamber 10 and pressure sensor 12 is arranged, whereby further in the container 14 a humidity sensor is located, which detects leaking fluid indicating defective sealing of the pressure-measuring system 8. If during the operation of injector 1 the counterpressure rises too much, respectively the pressure in the tube system increases too much, for instance due to a cannula with a diameter which is too small, so that the linear correlation between rotary speed of the roller pump 7 and the flow rate no longer exists, then the increased pressure is detected by the pressure-measuring system 8 with the electric pressure receiver, and the signal is sent to an evaluation unit controlling the rotary speed of the pump, whereby when the acceptable pressure threshold values are surpassed the rotary speed of the pump is reduced so that the pressure falls back below the threshold and the amount of fluid delivered to the patient can again be determined from the rotary speed of the pump. The evaluation unit also produces a warning signal indicating the decrease of the pump speed, so that a decision can be made whether to accept the necessary extension of the injection time in order to reach the desired volume, or to interrupt the examination.

What is claimed is:

1. Injector for applying fluids, particularly contrast media for X-ray or nuclear spin tomography, having a tube (3) as well as roller pump (7) at least partially surrounded in peripheral direction by the tube (3) for the transport of a fluid from a storage vessel (2) to a cannula, characterized in that a pressure chamber (10) connected with the interior of the tube (3) through an opening (9) in the tube wall is provided, which has a component (11) adjustable under the effect of the fluid pressure and which acts upon a pressure sensor (12).

2. Injector according to claim 1, characterized in that between two segments of the tube (3) a rigid pipe (13) with the opening (9) is inserted, the pressure chamber (10) being fastened to the same.

3. Injector according to claim 1, characterized in that the adjustable component (11) is formed by a liquid-proof elastic membrane.

4. Injector according to claim 1, characterized in that the adjustable component (11) is formed by a piston acting upon the pressure sensor (12) in cooperation with a prop tightened against the bottom of the pressure chamber (10).

5. Injector according to claim 1, characterized in that the adjustable component (11) is a piston tightened against the pressure-chamber wall acting directly upon the pressure sensor (12).

6. Injector according to claim 1, characterized in that the pressure chamber (10) and the thereto assigned pressure sensor (12) are provided twice.

7. Injector according to claim 1, characterized in that several openings (9) in the tube wall are assigned to the pressure chamber (10).

8. Injector according to claim 1, characterized in that the pressure chamber (10) is arranged on the cannula-side end of the tube (3).

9. Injector according to claim 1, characterized in that the tube (3) with the pressure chamber (10) and the pressure sensor (12) pass through a container (14) wherein a humidity sensor is arranged as a leak detector.

10. Injector according to claim 1, characterized in that the pressure sensor (12) is formed by an electric pressure receiver.

11. Injector according to claim 10, characterized in that an evaluation unit controlling the rotary speed of the pump is provided for the electric signals produced by the electric pressure receiver.

* * * * *